United States Patent
Teasdale et al.

(10) Patent No.: US 10,815,340 B2
(45) Date of Patent: Oct. 27, 2020

(54) POLYMER FOR TISSUE ENGINEERING

(71) Applicants: Universitat Linz, Linz (AT); Biomed-Zet Life Science GmbH, Linz (AT)

(72) Inventors: Ian Teasdale, Linz (AT); Sandra Rothemund, Rehau (DE); Tamara Aigner, Leonding (AT); Aiztiber Iturmendi, Linz (AT); Oliver Brueggemann, Wilhering (AT); Klaus Schroeder, Linz (AT); Gbenga Olawale, Linz (AT); Florian Hildner, Lasberg (AT); Maria Rigau De Llobet, Linz (AT)

(73) Assignees: UNIVERSITÄT LINZ, Linz (AT); BIOMED-ZET LIFE SCIENCE GmbH, Linz (AT)

(*) Notice: Subject to any disclaimer, the term of this patent is extended or adjusted under 35 U.S.C. 154(b) by 0 days.

(21) Appl. No.: 15/319,339

(22) PCT Filed: Jun. 16, 2015

(86) PCT No.: PCT/AT2015/050151
§ 371 (c)(1),
(2) Date: Dec. 21, 2016

(87) PCT Pub. No.: WO2015/192158
PCT Pub. Date: Dec. 23, 2015

(65) Prior Publication Data
US 2017/0183453 A1    Jun. 29, 2017

(30) Foreign Application Priority Data
Jun. 16, 2014 (AT) .............................. A 50416/2014

(51) Int. Cl.
*C08G 79/02* (2016.01)
*A61L 27/18* (2006.01)
(Continued)

(52) U.S. Cl.
CPC ............ *C08G 79/025* (2013.01); *A61L 27/18* (2013.01); *A61L 27/52* (2013.01); *A61L 27/56* (2013.01);
(Continued)

(58) Field of Classification Search
CPC ... C08G 78/025; C08G 2230/00; A61L 27/56; A61L 27/18; C08J 9/26; C08J 2207/10;
(Continued)

(56) References Cited

U.S. PATENT DOCUMENTS

| | | | |
|---|---|---|---|
| 6,235,061 B1 | 5/2001 | Laurencin et al. | |
| 2010/0297155 A1* | 11/2010 | Song ........................ | A61K 9/06 424/184.1 |

FOREIGN PATENT DOCUMENTS

| | | |
|---|---|---|
| EP | 2540764 | 1/2013 |
| GB | 2449264 | 11/2008 |

(Continued)

OTHER PUBLICATIONS

International Search Report in International Application No. PCT/AT2015/050151, dated Oct. 7, 2015, 6 pages.
(Continued)

*Primary Examiner* — Jessica M Roswell
(74) *Attorney, Agent, or Firm* — Liang & Hennessey LLP; Brian E. Hennessey

(57) ABSTRACT

The invention relates to a polymer for tissue engineering from biodegradable polyphosphazenes, having photopolymerizable side groups, wherein the side groups of the polyphosphazenes are formed exclusively from amino acids and/or amino acid derivatives, which are bonded to the
(Continued)

backbone of the polyphosphazene via the amino group of the amino acid and to a spacer attached to the acid group with a carbon chain of length m, which has a vinyl group at the free end, wherein m=0 to m=10.

20 Claims, 1 Drawing Sheet

(51) Int. Cl.
  *A61L 27/56* (2006.01)
  *C08J 9/26* (2006.01)
  *C08G 79/025* (2016.01)
  *C08L 85/02* (2006.01)
  *A61L 27/52* (2006.01)

(52) U.S. Cl.
  CPC .............. *C08G 79/02* (2013.01); *C08J 9/26* (2013.01); *C08L 85/02* (2013.01); *C08G 2230/00* (2013.01); *C08J 2201/0446* (2013.01); *C08J 2205/10* (2013.01); *C08J 2207/10* (2013.01); *C08J 2385/02* (2013.01)

(58) Field of Classification Search
  CPC .............. C08J 385/02; C08J 2201/0446; C08J 2201/22051; C08J 220/51
  See application file for complete search history.

(56) References Cited

FOREIGN PATENT DOCUMENTS

| WO | 2008153278 | 12/2008 | | |
|---|---|---|---|---|
| WO | WO 2008/153278 | * 12/2008 | ............ | C08G 79/02 |

OTHER PUBLICATIONS

Jung-Kyo Cho et al: "Synthesis and characterization of biodegradable thermosensitive neutral and acidic poly (organophosphazene) gels bearing carboxylic acid group", Journal of Polymer Research, Kluwer Academic Publishers-Consultants Bureau, NL, vol. 18, No. 4, Jul. 6, 2010 (Jul. 6, 2010), pp. 701-713.

* cited by examiner

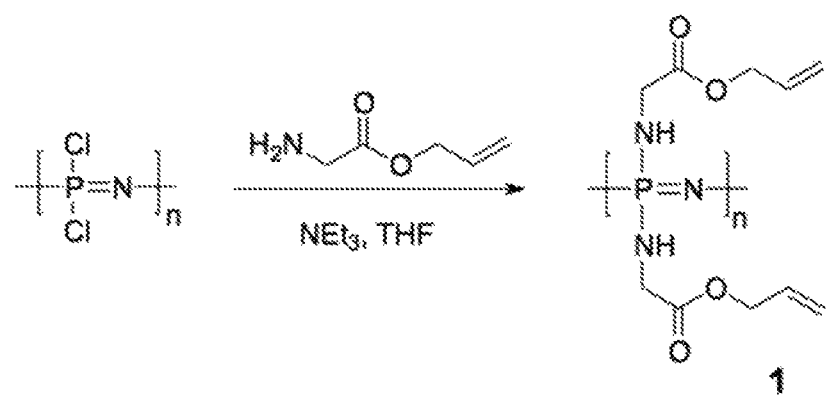

POLYMER FOR TISSUE ENGINEERING

The invention relates to a polymer for tissue engineering based on a biodegradable polyphosphazene, having photopolymerizable side groups, and to a three-dimensional scaffold for tissue engineering, using this polymer.

Advanced materials for biomedical applications, for example, for implants, delivery systems, controlled release of active ingredients, or scaffolds for tissue engineering are based on biodegradable polymers. Polymers that can be successfully used as matrices for tissue engineering are called for certain biological and physical properties such as biocompatibility, specific mechanical properties, adaptable degradation rates and non-toxic degradation products as well as a morphology that supports tissue growth. Poly(organo) phosphazenes are of particular interest for this scope of application due to their very different properties depending on the substituents of the side groups, but above all the possibility of changing the degradation rate of the inorganic backbone.

In addition, the degradation products form a nearly neutral, pH-buffered mixture of phosphates and ammonia, in contrast to acid degradation products from many other degradable polymers used in biomedicine, so that undesired side effects, such as tissue treatments and inflammatory or allergic reactions largely stay away.

In order to adjust the degradation rates of polyphosphazenes, it is known—U.S. Pat. No. 6,077,916—how to provide hydrophobic side groups such as p-methylphenoxy and other aromatic groups, and hydrolytic side groups such as amino acid alkyl esters. Thus, for example the hydrophobicity of a polyphosphazene substituted with ethylglycinate is increased by adding p-methylphenoxy as the co-substituent while the ethylglycinate side group provides the biological possibility to render harmless degradation products in an aqueous environment.

However, it is a disadvantage that the mechanical properties required for use in tissue engineering can only be achieved with an additional polymer that is not based on a polyphosphazene.

In order to provide highly porous, three-dimensional, biodegradable polymer structures based on polyphosphazenes for the cultivation of skeletal tissues, it is also known—U.S. Pat. No. 6,235,061—to substitute the polyphosphazene with hydrolytically unstable side groups such as glucosyl, glycinyl, glyceryl, imidazolyl, or ethoxy groups. The high porosity is made possible by salts, preferably sodium salts, which are admixed with the polymer dissolved in an organic solvent, preferably tetrahydrofuran (THF), in order to be dissolved again from the cured polymer after evaporation of the solvent so that an open-pore polymer matrix with pores can acquired, uniformly distributed over the volume of the pores. However, it is a disadvantage that the mechanical properties of these known polymer structures cannot meet the higher requirements when used as an implant.

Patent WO 2008153278 A1 shows polyphosphazene-based hydrogels, the polyphosphazene having cross-linkable side groups. The somewhat higher mechanical stability of the hydrogel which can be achieved by the cross-linking is of advantage. The polymer described has a disadvantage due to the polyphosphazene having several different side groups, which requires a complex production process. It is also a disadvantage that, due to the different side groups, a sufficiently high cross-linking is not achievable and due to the use of a PEG side group, a soft hydrophilic polymer results in a water-swelling hydrogel.

The invention is therefore based on the task of designing a polymer for tissue engineering of the type described at the outset in such a way that not only advantageous preconditions for an adjustable, biological degradation are created but also the prerequisites are created with the aid of these polymer structures in a simple manner for tissue engineering in well-suited, three-dimensional scaffolding, which can also meet higher mechanical requirements.

In order to solve the issue, a polymer for tissue engineering from biodegradable polyphosphazenes, having photopolymerizable side groups is proposed, in which the side groups of the polyphosphazenes are formed exclusively from amino acids and/or amino acid derivatives, which are bound to the backbone of the polyphosphazene by the amino group of the amino acid and a vinyl group on the acid group bonded via a spacer, that is a reactive carbon-carbon double compound, wherein for the length m of the carbon chain of the spacer m=0 to m=10.

It is particularly advantageous that each side group has a reactive carbon double compound at the end, resulting in an improved cross-linkable polymer. Cross-linking allows rigid, dimensionally stable scaffolds for tissue engineering to be produced, which can have a high porosity. It is also particularly advantageous that all side groups bind via the peptide bond of the amino group of the amino acids, or of the amino acid derivatives on the polyphosphazene backbone, as a result of the uniform reactivity with binding of the side groups, thus the production process can be easily controlled, particularly also when different amino acid or amino acid derivative side groups of the quantitative ratio of such are used.

The cross-linkable polyphosphazene according to the invention preferably has a structure according to the structural formula

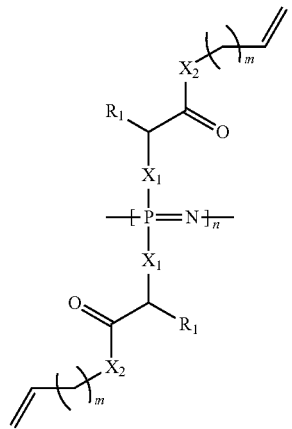

wherein $X_1$ stands for NH and $X_2$ stands for O, S or NH, $R_1$ is the side chain of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutainyl, aspartoyl, glutaoyl, lysinyl, arginino or histidinyl, and wherein m=0 to 10 and n=3 to 1000.

The side group of the polyphosphazene is preferably an amino acid ester, more preferably an amino acid vinyl ester or an amino acid allyl ester. Accordingly, the vinyl group or their spacer is bonded to the hydroxy group of the amino acid via an ester bond ($X_2$ stands for O).

When an amino acid derivative is used, an amide ($X_2$ stands for NH) or a thioester bond ($X_2$ stands for S) may be present instead of the ester bond.

A polyphosphazene according to the invention can have side groups of different amino acid esters or amino acid derivatives, for example valine allyl esters and glycine allyl esters, preferably the polyphosphazene according to the invention has uniform side groups, for example exclusively glycine allyl esters.

It is also conceivable to replace the amide bond $X_1$ with an ester or thioester bond ($X_1$ would stand for O or S), but this would lead from the current viewpoint to a polymer with rather disadvantageous properties for the preferred application as a scaffold for tissue engineering.

Due to the side groups, the comparatively short-chain polyphosphazene can be subjected to photopolymerization with the result of a pronounced cross-linking with covalent bonds, so that all prerequisites for producing a three-dimensional, cross-linked polymer backbone are fulfilled which brings about the mechanical properties for an implantable scaffold for tissue engineering, being biocompatible and biodegradable.

The incorporation of amino acid spacers adjacent to the backbone, such as preferably glycine spacers, particularly accelerates the hydrolytic degradability of the polyphosphazene backbone, the reactive carbon-carbon double compound of the vinyl group at the end of each side group, providing advantageous prerequisites for the subsequent photochemical cross-linking and functionalization of the polymer.

Three-dimensional scaffolds for tissue engineering can be produced particularly advantageously on the basis of polyphosphazenes substituted with amino acid vinyl esters or amino acid allyl esters if the polyphosphazene is photopolymerized or photo-cross-linked.

A thiol compound, having at least two thiol groups can advantageously be used for the photoreaction, the use of a corresponding selection of multifunctional thiols with different spacers between the two or more thiol groups, the adaptation of the respective properties to the predetermined requirements and the control of the hydrophilic and hydrophobic behavior of the finished scaffold. Particularly advantageous conditions have been ensured in this context if a thiol-trimethylolpropane tris (3-mercaptopropionate), having three thiol groups, is used as the thiol compound. Functionalization via an addition of thiol-ene allows the covalent bonding of various molecules with a thiol group. Thus, the biodegradability of the polymer backbone can be influenced in a sustained manner by the polymerization of the polyphosphazene with a thiol compound and an adipic acid divinyl-ester, owing to the hydrophobicity of this ester. The properties of the three-dimensional, cross-linked scaffold can thus be easily adjusted, requiring only the synthesis of a single poly(organo)phosphazene with uniform side groups.

The required porosity of the three-dimensional scaffold for tissue engineering can be achieved in various ways in a manner known per se, for example by stereolithography or by foaming a propellant gas. Particularly simple production conditions are obtained however when a porogen, preferably a salt, is added to the cross-linking components, which after the polymerization is leached out of the polymer again and leaves a coherent pore system.

The invention is illustrated by means of a manufacturing example and a drawing:

FIG. 1: Shows the reaction scheme for the preparation of an exemplary polyphosphazene, having polymerizable side groups according to the invention.

To prepare a polyphosphazene according to the invention, a macromolecular substitution of polydichlorophosphazene was carried out, synthesized by a living polymerization of trichlorophosphoranimine. 24.5 mg of $PCl_5$ (0.12 mmol, 1 eq.) and 0.66 g of $Cl_3P=N-SiMe_3$ (2.94 mmol, 25 eq.) were dissolved in 10 ml of anhydrous $CH_2Cl_2$ in the glove box and stirred at room temperature for 16 hours. The solvent was removed under reduced pressure, and the resulting polydichlorophosphazene was used without further purification.

Yield quantitative: $^{31}$P-NMR (CDC13): δ=−18.16 ppm.

The macromolecular substitution of polydichlorophosphazene was carried out according to the method showed in FIG. 1, the polymer obtained with 1 side groups of glycine allyl esters.

First, 1.52 g of 2-(tert-butoxycarbonylamino) acetate (7.06 mmol, 2.4 eq) in trifluoroethanoic acid (TFA)/$CH_2Cl_2$ (⅓) was deprotected for 6 hours. The solvents were carefully removed under vacuum to obtain allyl-2-aminoacetate. Allyl-2-aminoacetate was dissolved in anhydrous THF and a large excess of NEt3 was added to neutralize TFA residues. Polydichlorophosphazene (0.66 g, 2.94 mmol, 1 eq.), dissolved in anhydrous THF, was then added to the solution of allyl-2-aminoacetate. The reaction was stirred at room temperature for 24 hours. Precipitated salt was removed by filtration and the reaction mixture was concentrated under vacuum. The polymer was purified by precipitation from THF in cooled diethyl ether. The polymer was then dissolved in ethyl acetate and further washed with $H_2O$ and a brine and dried over $MgSO_4$. The solvent was removed under vacuum and the product was further dried under high vacuum to obtain the polymer 1 as a yellowish highly viscous product.

Yield: 0.66 g (80%). $^1$H-NMR (CDCl$_3$): δ=3.75 (br, 2H), 4.55 (br, 2H), 5.19 to 5.31 (br, m, 2H), 5.84 to 5.93 (br, m, 1H) ppm. $^{31}$P-NMR (CDCl$_3$): δ=1.73 ppm. $^{13}$C-NMR (CDCl$_3$): δ=42.8 (NH—CH$_2$), 65.5 (OCH$_2$), 118.4 (—CH$_2$), 132.2 (—CH—), 172.5 (C—O) ppm. FTIR (solid): $v_{max}$=3341 (NH), 2938 (CH), 1737 (C=O), 1650 (C=C), 1188 (P=N) cm$^{-1}$.

In order to obtain a porous, three-dimensional scaffold based on glycine, the polymer 1 was cross-linked by thiol-ene-photopolymerization with thiol trimethylolpropane tris (3-mercaptopropionate), hereinafter referred to as tri-thiol. The photopolymerization of the allyl groups of the polymer 1 and the tri-thiol was carried out in small amounts (about 1 wt %) as a photo-initiator at room temperature in the presence of a porogen in CHCl$_3$ with 2,2-dimethoxy-2-phenylacetophenone (DMPA). In a glass vial, polymer 1 (90.0 mg, 0.33 mmol, 1 eq.) and 1 mg were dissolved in 1 ml of CHCl$_3$. Then, 0.5 ml of polyethylene glycol with a nominal molecular weight of 200 g/mol (PEG-200), tri-thiol (72 μl, 87.6 mg, 0.22 mmol, 0.67 eq) and NaCl as porogen (c. 4.2 g, 75 wt % of the reaction mixture) was added to obtain a homogeneous mixture with fully dispersed NaCl particles.

The mixture was exposed to ultraviolet light in a UV reactor for 1.5 hours.

The material was removed from the vial and repeatedly washed into a $H_2O$ excess to wash out the salt and the PEG-200. The scaffolds were purified by soxhlet extraction, using EtOH for 16 hours, and dried under vacuum to obtain a polymer 2 as a porous pellet. The solidification of the reaction mixture showed a successful formation of the cross-linked polymer network around the porogen.

Result: $^{31}$P-NMR (solid): δ=7.7 ppm. $^{13}$C-NMR (solid): δ=7.6 (CH$_3$), 26.8 (CH$_2$), 43.8 (NH—CH$_2$), 65.1 (OCH$_2$), 172.1 (C—O) ppm. FTIR (solid): $v_{max}$=3342 (NH), 2926 (CH), 1729 (C=O), 1188 (P=N) cm$^{-1}$. Elementary analysis: calculated, C, 44.57%; H, 6.23%; N, 7.80%; S, 11.90%; P, 5.75%. found, C, 43.97%; H, 6.21%; N, 7.08%; S, 11.23%; P, 5.47%.

The polymer 1 was also mixed with a commercially available adipic acid vinyl ester (VE) in various proportions to change the degradation rates of the obtained scaffolds. The conditions for the thiol-ene-cross-linking reaction were similar to the thiol-ene-cross-linking reaction of the polymer 1 in an adjustment of the molar ratio of the alkene groups to the thiol groups (1/1).

For a polymer 3, 27 wt % of the polymer 1 was mixed with 53 wt % of tri-thiol and 20 wt % of deionized water and subjected to a thiol-ene-cross-linking reaction.

Result: FTIR (solid): $v_{max}$=3353 (NH), 2930 (CH), 1728 (C=O), 1184 (P=N) cm-1.

Analysis: calculated, C, 47.91%; H, 6.50%; N, 4.19%; S, 12.79%; P, 3.09%. found, C, 47.50%; H, 6.54%; N, 4.17%; S, 12.36%; P, 3.25%.

The degradation studies were carried out in deionized $H_2O$ at 37° C. for 12 weeks. Samples containing 30 mg of Polymers 2 and 3 were placed in sealed vials and incubated in 2 ml of $H_2O$. A data analysis was carried out three times at appropriate intervals over the examination period.

The samples were dried in a vacuum oven at 40° C. until the weight was constant. The mass loss was determined gravimetrically, wherein the respective established average value of the mass losses as a percentage compared to the initial weight of the degradation sample are shown in the following table.

|  | Loss of Weight [in %] after | | | | | |
| --- | --- | --- | --- | --- | --- | --- |
|  | 10 Days | 20 Days | 42 Days | 56 Days | 90 Days | 120 Days |
| Polymer 2 | 5 | 16 | 33 | 60 | 62 | 85 |
| Polymer 3 | 0 | 0 | 7 | 7 | 20 | 26 |

The table shows that the polymer 2, which had the highest proportion of polyphosphazenes exhibited a pronounced degradation profile in a neutral aqueous solution at 37° C. As a result of the hydrolytic degradation of the polyphosphazene backbone, the network bonds of the cross-linked organic mass are separated, which leads to an improvement in the overall biodegradation rates of the scaffold. With the decrease of the polyphosphazene content and the increase of the adipic acid vinyl ester, the degradation rate is considerably reduced which is attributed to the increased hydrophobicity.

Due to the preferred application of the three-dimensional scaffolds for tissue engineering according to the invention, the cytotoxicity of these scaffolds was investigated in conjunction with primary epithelial cells and stem cells (ASC) obtained from adipose tissue, whereby no cytotoxicity could be detected for cells in a medium previously treated with a polymer 2, which has a particularly high proportion of polyphosphazenes. Furthermore, preliminary studies also showed no cytotoxicity of polymer 2 in a cell culture medium at 37° C. for a period of 42 days in which 33% of the polymer had already been degraded, suggesting the non-toxicity of degradation products or their intermediates.

The invention claimed is:

1. A polymer for tissue engineering, comprising:
   biodegradable polyphosphazenes, having photopolymerized side groups, wherein the side groups of the polyphosphazenes are formed exclusively from amino acids and/or amino acid derivatives, each having a vinyl group at the free end prior to crosslinking of the side groups and which are bonded to the backbone of the polyphosphazene via the amino group of the amino acid and have a spacer on the acid group, which carbon chain is present with the length m=0 to m=10, which has said vinyl group at the free end, wherein said side groups are crosslinked via said vinyl groups at the free ends of said side groups,
   wherein each polyphosphazene of the polymer, prior to crosslinking of said side groups, conform to the structural formula

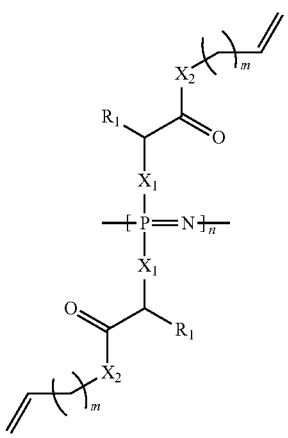

wherein $X_1$ stands for NH and $X_2$ stands for O, S or NH, and $R_1$ is the side chain of alanyl, valinyl, leucinyl, isoleucinyl, prolinyl, phenylalaninyl, tryptophanyl, methioninyl, glycinyl, serynyl, threoninyl, cysteinyl, tyrosinyl, asparaginyl, glutainyl, aspartoyl, Glutaoyl, lysinyl, arginine or histidinyl, and m=0 to 10 and n=3 to 1000.

2. A polymer as claimed in claim 1, wherein said side groups prior to crosslinking of said side groups are formed from amino acid vinyl ester or amino acid allyl ester.

3. A polymer as claimed in claim 1, wherein said vinyl groups of said side groups prior to crosslinking are joined by thiol compounds when performing crosslinking of said side groups, said thiol compounds having at least two thiol groups.

4. A polymer as claimed in claim 3, wherein, when performing crosslinking of said side groups, adipic acid divinyl esters are cross-linked to said vinyl groups, which are present prior to crosslinking of said side groups, with said thiol compounds with said at least two thiol groups.

5. A polymer as claimed in claim 3, wherein said thiol compound has three thiol groups.

6. A polymer as claimed in claim 1, wherein the polymer has homogeneously distributed leachable porogen included in its polymer matrix.

7. A polymer as claimed in claim 1, wherein the polymer is a three-dimensional scaffold of a desired form or shape by bringing the vinyl capped polyphosphazenes into the desired form or shape and performing photopolymerization or photo-cross-linking.

8. A polymer as claimed in claim 7, wherein said three-dimensional scaffold composed of said photopolymerized or photo-cross-linked polymer is rigid and porous.

9. A polymer for tissue engineering, comprising:
   biodegradable polyphosphazenes, having photopolymerized side groups, wherein the side groups of the polyphosphazenes are formed exclusively from amino acids and/or amino acid derivatives, each having a vinyl group at the free end prior to crosslinking of the side groups and which are bonded to the backbone of the polyphosphazene via the amino group of the amino acid and have a spacer on the acid group, which carbon chain is present with the length m=0 to m=10, which has said vinyl group at the free end, wherein said side groups are crosslinked via said vinyl groups at the free ends of said side groups, wherein said vinyl groups of said side groups prior to crosslinking are joined by thiol compounds when performing crosslinking of said side groups, said thiol compounds having at least two thiol groups, and wherein, when performing crosslinking of said side groups, acid divinyl esters are cross-linked to said vinyl groups, which are present prior to crosslinking of said side groups, with said thiol compounds with said at least two thiol groups.

10. A polymer as claimed in claim 9, wherein each polyphosphazene of the polymer, prior to photopolymerization or photo-cross-linking conform to the structural formula

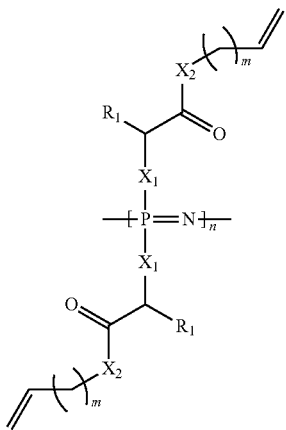

wherein $X_1$ stands for NH and $X_2$ stands for O, S or NH, and $R_1$ is the side chain of alanyl, valinyl, leucinyl, isoleucinyl, prolinyl, phenylalaninyl, tryptophanyl, methioninyl, glycinyl, serynyl, threoninyl, cysteinyl, tyrosinyl, asparaginyl, glutainyl, aspartoyl, Glutaoyl, lysinyl, arginine or histidinyl, and m=0 to 10 and n=3 to 1000.

11. A polymer as claimed in claim 9, wherein said side groups, prior to crosslinking of said side groups, are formed from amino acid vinyl ester or amino acid allyl ester.

12. A polymer as claimed in claim 9, wherein said vinyl groups, which are present prior to crosslinking of said side groups, are joined by thiol compounds when performing crosslinking of said side groups, said thiol compounds having at least two thiol groups.

13. A polymer as claimed in claim 12, wherein said polymer comprises adipic acid divinyl esters, said adipic acid divinyl esters are cross-linked to said vinyl groups, which are present prior to crosslinking of said side groups, with said thiol compounds with said at least two thiol groups when performing crosslinking of said side groups.

14. A polymer as claimed in claim 12, wherein said thiol compound has three thiol groups.

15. A polymer as claimed in claim 8, wherein pores are formed by washing out a homogeneously distributed leachable porogen which is included in the polymer matrix of the photo-polymerized polymer.

16. A polymer as claimed in claim 9, wherein said thiol compound is a trimethylolpropane tris (3-mercaptopropionate).

17. A polymer as claimed in claim 6, wherein said porogen is a salt.

18. A polymer as claimed in claim 1, wherein the polymer is dimensionally stable.

19. A polymer as claimed in claim 9, wherein said polymer comprises additional molecules, said molecules are covalently bonded to a thiol group of said thiol compounds with said at least two thiol groups.

20. A polymer for tissue engineering, comprising:
biodegradable polyphosphazenes, having photopolymerized side groups, wherein the side groups of the polyphosphazenes are formed exclusively from amino acids and/or amino acid derivatives, each having a vinyl group at the free end prior to crosslinking of the side groups and which are bonded to the backbone of the polyphosphazene via the amino group of the amino acid and have a spacer on the acid group, which carbon chain is present with the length m=0 to m=10, which has said vinyl group at the free end, wherein said side groups are crosslinked via said vinyl groups at the free ends of said side groups, wherein the polymer is a three-dimensional scaffold of a desired form or shape by bringing the vinyl capped polyphosphazenes into the desired form or shape and performing photopolymerization or photo-cross-linking, and wherein each polyphosphazene of the polymer, prior to photopolymerization or photo-cross-linking conform to the structural formula

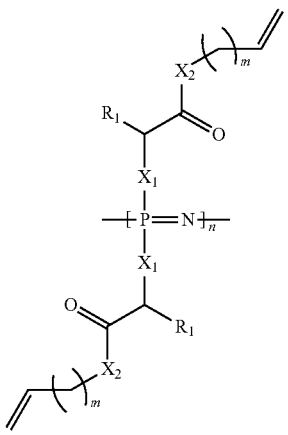

wherein $X_1$ stands for NH and $X_2$ stands for O, S or NH, and $R_1$ is the side chain of alanyl, valinyl, leucinyl, isoleucinyl, prolinyl, phenylalaninyl, tryptophanyl, methioninyl, glycinyl, serynyl, threoninyl, cysteinyl, tyrosinyl, asparaginyl, glutainyl, aspartoyl, Glutaoyl, lysinyl, arginine or histidinyl, and m=0 to 10 and n=3 to 1000.

* * * * *